United States Patent [19]

Olson et al.

[11] 3,960,967

[45] June 1, 1976

[54] PROCESS FOR PRODUCING A SULFONE DERIVATIVE OF VITAMIN A ALCOHOL

[75] Inventors: Gary Lee Olson, Westfield; Gabriel Saucy, Essex Fells, both of N.J.

[73] Assignee: Hoffmann-La Roche Inc., Nutley, N.J.

[22] Filed: July 19, 1974

[21] Appl. No.: 486,145

Related U.S. Application Data

[63] Continuation-in-part of Ser. No. 398,713, Sept. 14, 1973, abandoned.

[52] U.S. Cl............................ 260/607 R; 260/397.6; 260/563 R
[51] Int. Cl.²...................................... C07C 147/02
[58] Field of Search................................ 260/607 A

[56] References Cited
UNITED STATES PATENTS 3,781,313   12/1973   Julia................................ 260/607 A
3,803,252   4/1974   Chabardes et al............. 260/607 A
3,848,000   11/1974   Chabardes et al............. 260/607 A
3,850,991   11/1974   Chabardes et al............. 260/607 A Primary Examiner—Lewis Gotts
Assistant Examiner—D. R. Phillips
Attorney, Agent, or Firm—Samuel L. Welt; Bernard S. Leon; William H. Epstein

[57] ABSTRACT

A process for the preparation of vitamin A and esters thereof from the condensation of a sulfone of 2-methyl-4-hydroxy-but-2-ene and an activated derivative of 3-methyl-5-(2,6,6-trimethyl-cyclohexen-1-yl)penta-2,4-diene including intermediates therein.

2 Claims, No Drawings

PROCESS FOR PRODUCING A SULFONE DERIVATIVE OF VITAMIN A ALCOHOL

CROSS REFERENCE TO RELATED APPLICATIONS

This application is a continuation in part application of U.S. application Ser. No. 398,713 filed Sept. 14, 1973 now abandoned.

BACKGROUND OF THE INVENTION

In the past, sulfone condensation has been carried out with acid derivatives having an activated leaving group on the carbon atom. See German Offlegungschrift 2,202,689, Aug. 3, 1972 and U.S. Pat. No. 3,804,882, Apr. 16, 1974. However, this procedure has not been advantageous in the production of vitamin A alcohol or esters thereof since the product formed is a vitamin A acid derivative. These vitamin A acid derivatives require various reaction steps to form vitamin A alcohol or derivatives thereof. The use of these reaction steps involve additional expense and loss of yield which make the sulfone condensation not commercially attractive in the production of vitamin A alcohol or esters thereof. Therefore, a simple and economic procedure has been desired for directly converting a sulfone to an alcohol or derivative thereof such as vitamin A alcohol or esters thereof. Such a procedure would eliminate the various steps necessary to convert vitamin A acid to vitamin A alcohol and the economic disadvantages inherent in these steps.

SUMMARY OF THE INVENTION

In accordance with this invention, it has been unexpectedly discovered that a sulfone of the formula:

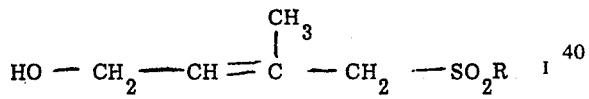

wherein R is unsubstituted aryl or aryl substituted with an electron donating group;
can be alkylated with a derivative of the formula:

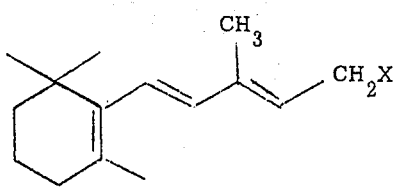

wherein X is a leaving group; to produce a compound of the formula:

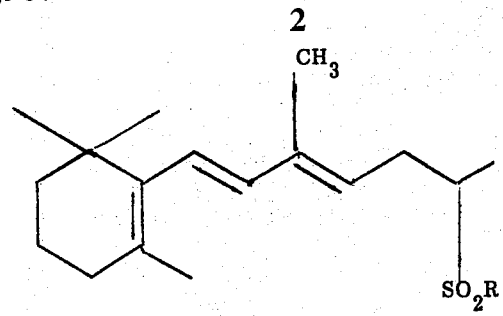

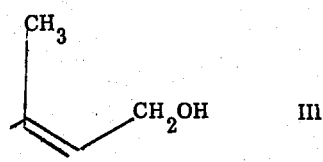

wherein R is above
which upon treatment with a base yields vitamin A alcohol having the formula:

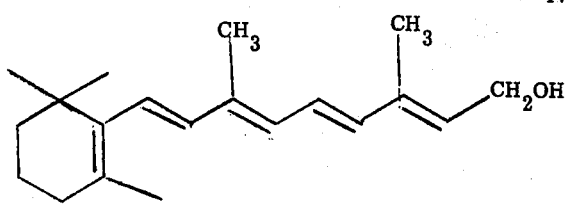

It has been found that the double bond in the compound of formula IV formed by alkylating the compound of formula I with the compound of formula II followed by elimination of the sulfone has a trans configuration. This is extremely advantageous in the production of vitamin A alcohol, since the commercial product is the all trans isomer. When the double bonds in the compounds of formula I and II have a trans configuration, this synthesis will produce vitamin A alcohol and esters thereof with an all trans configuration without the need for separate isomerization or purification steps with consequent loss of yield. The procedure of this invention provides a direct method for producing all trans vitamin A alcohol or derivatives thereof by sulfone alkylation without forming acids such as vitamin A acid and derivatives thereof. This procedure eliminates steps necessary to convert this vitamin A acid into vitamin A alcohol.

In accordance with this invention, R in the compound of formula I, is unsubstituted aryl, preferably phenyl, or aryl substituted with an electron donating group. The electron donating groups for use in this invention have Hammett $\sigma$ values of from 0 to $-1.0$ as set forth in the tables on pages 145 and 146 in Gordon and Ford "The Chemist's Companion," John Wiley and Sons, (1972). Among these groups are included hydrogen, lower alkyl, lower alkoxy, carboxy, hydroxy, aryloxy, amino and alkyl amino. If an electron accepting group is substituted on the aryl moiety such as those with a positive Hammett σ value (greater than zero), the conversion of the compound of formula I to the compound of formula III and the conversion of the compound of formula III to the compound of formula IV, occurs, if at all, in very low yields. On the other hand, where the substituent on the phenyl moiety which forms R is hydrogen or an electron donating group, these conversions proceed to produce vitamin A alcohol with a trans configuration in high yields.

Among the preferred compounds of formula I are compounds having the formula:

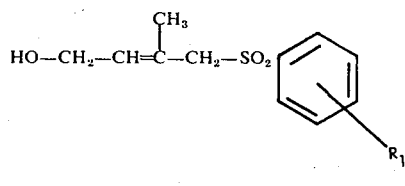

wherein
R$_1$ is hydrogen, lower alkyl, hydroxy, lower alkoxy, phenoxy, or

R$_4$ and R$_5$ are hydrogen or lower alkyl.

Detailed Description of the Invention

As used throughout this application, the term "lower alkyl" includes both straight chain and branched chain alkyl groups having from 1 to 7 carbon atoms such as methyl, ethyl, propyl, isopropyl, and n-butyl. As used throughout this application, the term "lower alkoxy" comprehends lower alkoxy groups having from 1 to 7 carbon atoms such as methoxy and ethoxy. The term "lower alkanoyl" designates lower alkanoyl groups containing from 2 to 7 carbon atoms such as acetyl, propionyl, etc. The term "lower alkyl amino" includes both mono- and di-lower alkyl amino groups such as methyl amino, ethyl amino, dimethyl amino, methylethyl amino, etc.

As also used herein, the term "lower alkanoic acid" comprehends an alkanoic acid of from 2 to 7 carbon atoms such as propionic acid and acetic acid. As further used herein, the term "halogen" or "halo", unless otherwise stated, comprehends fluorine, chlorine, bromine and iodine. The term "alkali metal" includes sodium, potassium, lithium, etc.

As also used herein, the term "unsubstituted aryl" signifies mono nuclear aromatic hydrocarbon groups such as phenyl and polynuclear aryl groups such as naphthyl, anthryl, phenanthryl, etc. The preferred aryl group is phenyl. The term "aralkyl" denotes aryl lower alkyl groups wherein aryl and lower alkyl are defined as above, particularly benzyl. The term "aryl lower alkanoic acid" comprehends acids wherein "aryl" and "lower alkanoic acid" are defined as above, particularly phenyl acetic acid. The term "aroyl" denotes aroyl groups wherein the aryl group is defined as above. The preferred aroyl substituents are benzoyl or phenyl benzoyl.

As used herein, the term "hydroxy protected by a hydrolyzable ester group" designates any ester group which can be hydrolyzed to yield the hydroxy group. Exemplary ester groups useful for this purpose are those in which the acyl moiety is derived from a lower alkanoic acid, an aryl lower alkanoic acid such as benzoic acid, an aroic acid, or a lower alkane dicarboxylic acid. Among the acid derivatives which can be utilized to form such ester groups are the acid anhydrides and the acid halides, preferably chloride or bromide, with the lower alkanoic acid anhydrides, e.g., acetic anhydride, caproic anhydride the aryl lower alkanoic acid anhydrides, e.g., benzoid acid anhydrides, lower alkane dicarboxylic acid anhydrides, e.g., succinic anhydrides and the chloroformates, e.g., trichloroethylchlorformate, being preferred.

Among the preferred compounds of formula I are compounds having the formula:

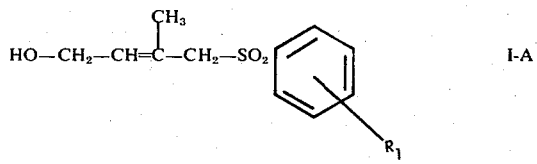   I-A wherein
R$_1$ is hydrogen, lower alkyl, hydroxy, lower alkoxy, phenoxy, or

R$_4$ and R$_5$ are hydrogen or lower alkyl.

In the first step of the process of this invention, a sulfone of the formula I is condensed with a compound of the formula II to produce a compound of the formula III. In the compound of the formula II, X can be any conventional leaving group. Among the preferred leaving groups are included lower alkyl sulfonyloxy such as methyl sulfonyloxy; arylsulfonyloxy such as p-toluenesulfonyloxy; or halogen. The preferred leaving group is halogen such as bromine, chlorine or iodine.

The reaction of the compound of formula II with the compound of formula I is carried out in the presence of a strong base. Among the strong bases which can be utilized are alkali metal alcoholates such as sodium methoxide, sodium ethoxide, alkali metal hydrides such as sodium hydride, lithium compounds such as phenyl lithium as well as an alkali metal amide of the formula:

   X wherein
M is an alkali metal and R$_{10}$ and $R_{11}$ are hydrogen or lower alkyl.

In carrying out this reaction, the preferred base is the compound of formula X. Among the preferred bases of formula X are included sodamide, lithium diisopropylamide, sodium diisopropylamide and lithium ethylamide. In carrying out this reaction, any conventional inert organic polar solvent can be utilized. Among the preferred polar solvents are included dimethyl sulfoxide and ethers such as tetrahydrofuran, diethyl ether, dioxane, etc. The polar solvents can be utilized either alone or mixed with a non-polar solvent. The non-polar solvents which forms the mixture with the polar solvent can be any conventional non-polar solvent such as benzene, hexane, toluene, cyclohexane, etc. If desired, the solvent medium can contain from about 5 to 95% by volume of the polar solvent with the remainder being any conventional inert organic solvent. In carrying out this reaction, temperatures of from $-100°$ to $0°$ C. are utilized with temperatures of from about $-80°$ to $10°$ C. being preferred. In carrying out this reaction, generally at least one mole of the base is utilized per mole of the compound of formula I. Generally, it is preferred to utilize from 1.5 to 5 moles of the base per mole of the compound of formula I with amounts of from 1.5 to 4 moles being particularly preferred. However, amounts of above 5 moles of the base per mole of the compound of formula I can be utilized, if desired. However, since there are no additional beneficial results from utilizing such large quantities of base, the use of such large excess is seldom desired.

The compound of formula III is converted to the compound of formula IV by treating the compound of formula III with an inorganic base or a base of the formula X. In this reaction, any conventional base such as the bases mentioned above as well as alkali metal hydroxides which include sodium hydroxide, potassium hydroxide, etc., and the alkaline earth metal hydroxides such as calcium hydroxide can be utilized. This reaction, is carried out at a temperature of from $-80°$ to $160°C$. In this reaction, the inorganic base or the base of the formula X can be present in an amount of at least 1 mole per mole of the compound of formula III. Generally, it is preferred to utilize in this reaction from about 2 moles to about 25 moles of either the inorganic base or the base of the formula X per mole of the compound of formula III. While amounts of base in excess of 25 moles per mole of the compound of formula III can be utilized without adversely affecting the reaction, large amounts are seldom utilized due to the fact that little additional beneficial results are produced from utilizing such large amounts.

The solvent utilized as the reaction medium in this reaction is a polar solvent such as liquid ammonia, lower alkylamine, water, or a lower alkanol. On the other hand, the solvent medium can contain a mixture of the polar solvent with a conventional inert organic solvent. If desired, the solvent medium can contain from about 5 to 95% by volume of the polar solvent with the remainder being a conventional inert organic solvent. Any conventional inert organic solvent can be utilized in the reaction medium with ethers such as diethyl ether being preferred. Where it is desired to carry out the reaction at elevated temperatures, high boiling solvents, i.e., solvents having a boiling point greater than $80°$ C. can be utilized such as n-butanol and hexanol and the reaction can be carried out at atmospheric pressure. On the other hand, when it is desired to carry out the reaction at low temperatures, low boiling solvents such as methanol, ethanol and liquid ammonia may be utilized and this reaction can be carried out at the boiling temperature of the solvent. Alternatively, low boiling solvents can be utilized at high temperatures under pressure. The compound of formula IV can, if desired, be converted to a desired vitamin A ester such as vitamin A acetate by conventional methods of esterification.

The compound of formula I can be prepared by reacting a compound of the formula:

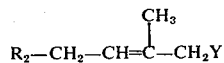

wherein
Y is a halide; preferable chlorine or bromine; and
$R_2$ is hydroxy protected with a hydrolyzable ester group;
with a salt of the formula:

wherein
M is an alkali metal and R is as above; to form a compound of the formula:

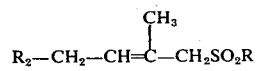

wherein
$R_2$ and R are as above.

The reaction of the compound of formula V with a compound of formula VI to form a compound of the formula VII can take place in a polar solvent. In carrying out this reaction, any conventional polar solvent can be utilized with solvents such as ethanol, methanol, dimethylformamide, hexamethylphosphoramide or dimethylsulfoxide being preferred. If desired, any conventional inert organic solvent can be present in this reaction medium in conjunction with the polar solvent. In carrying out this reaction, temperature and pressure are not critical and this reaction can be carried out at room temperature and atmospheric pressure. On the other hand, elevated or reduced temperatures can be utilized. Generally, it is preferred to carry out this reaction at a temperature of from $20°$ to $120°C$.

The compound of formula VIII can be converted to the compound of formula I by ester hydrolysis and where $R_2$ is hydroxy protected by a hydrolyzable ester group. Any conventional method of ester hydrolysis can be utilized to affect this conversion.

The invention is further illustrated by the following examples which are illustrative but not limitative thereof. All percents in these examples are percents by weight. The ether utilized is diethyl ether and the temperature is in degree centigrade.

EXAMPLE 1

Preparation of 1-phenylsulfonyl-2-methyl-4-acetoxy-but-2-ene

To a suspension of 24.2 g. of sodium benzenesulfinate in 150 ml. of dimethylformamide (DMF) was added 19.9 g. of 1-chloro-2-methyl-4-acetoxybut-2-ene in 50 ml. of DMF. The mixture was then heated to $60°C$. for 4.5 hours. A second portion, 19.0 g. of sodium benzenesulfinate was added and the heating continued for 1.5 hours. The reaction mixture was poured into 1.5 l. of water and filtered to remove the solid which was dissolved in 500 ml. of ethyl acetate. This solution was washed with three 300 ml. portions of water and dried over magnesium sulfate. Evaporation of the solvent afforded 25.2 g. of crude sulfone acetate, m.p. 86°–92°C. Ethyl acetate extraction, washing and drying of the aqueous filtrate afforded an additional 6.07 g. of less pure product. Recrystallization of the main portion from ethyl acetate gave analytically pure 1-phenylsulfonyl-2-methyl-4-acetoxy-but-2-ene, m.p. 93°–94°C.

EXAMPLE 2

Preparation of 1-phenylsulfonyl-2-methyl-4-hydroxy-but-2-ene

To a stirred suspension of 1.30 g. of lithium aluminum hydride in 100 ml. of tetrahydrofuran (THF) at −20°C. was added a solution of 1-phenylsulfonyl-2-methyl-4-acetoxy-but-2-ene in 50 ml. of tetrahydrofuran over a 20 minute period. The suspension was stirred for 25 minutes at −20°C. and warmed to −10°C. over 15 minutes. Saturated aqueous magnesium sulfate solution (20 ml.) was cautiously added to quench the reaction, followed by anhydrous magnesium sulfate. The suspension was filtered and concentrated at reduced pressure and the residue dissolved in 100 ml. of ethyl acetate. The ethyl acetate solution was washed with water, dried (MgSO$_4$), and evaporated to afford 12.2 g. of crystalline 1-phenylsulfonyl-2-methyl-4-hydroxy-but-2-ene. Recrystallization from ethyl acetate gave a pure white solid, m.p. 55°–56.5°C.

EXAMPLE 3

A 95% by weight aqueous methanolic solution of the 1-phenylsulfonyl-2-methyl-4-acetoxy-but-2-ene (0.204 g.) was stirred at room temperature with 0.518 g. of sodium carbonate for 35 minutes. Water was added and the mixture extracted with ethyl acetate. The extracts were washed with water, dried, and concentrated to give 0.14 g. of 1-phenylsulfonyl-2-methyl-4-hydroxy-but-2-ene containing approximately 25% by weight of 1-phenylsulfonyl-2-methylbutadiene as shown by nmr.

EXAMPLE 4

A 90% by weight aqueous methanolic solution of the 1-phenylsulfonyl-2-methyl-4-acetoxy-but-2-ene (0.205 g.) was stirred at room temperature for 3 hours and then refluxed for 1½ hours with 0.132 g. of sodium bicarbonate. Dilution of the reaction mixture with water and isolation with ethyl acetate as described in Example 3 afforded 0.114 g. of the 1-phenylsulfonyl-2-methyl-4-hydroxy-but-2-ene containing in this case, approximately 55% of the diene impurity.

EXAMPLE 5

Preparation of 1-hydroxy-3,7-dimethyl-4-(phenylsulfonyl)-9-(2,6,6-trimethylcyclohexen-1-yl)-none-2,6,8-triene A solution of n-butyllithium in hexane (46.5 ml., 1.95 M) was added over 45 minutes to a solution of 10.4 g. of 1-phenyl sulfonyl-2-methyl-4-hydroxy-but-2-ene in 200 ml. of tetrahydrofuran at −65° to −70°C. The reaction mixture was stirred at −70°C. for 40 minutes and a solution of 1-chloro-3-methyl-5-(2,6,6-trimethylcyclohexen-1-yl)-penta-2,4-diene in 45 ml. of THF was added over 10 minutes at −65° to −70°C. The solution was stirred at this temperature for one hour and then raised to 0°C. over 15 minutes. The reaction mixture was then poured into 250 ml. of 4% by weight aqueous hydrochloric acid and extracted with ethyl acetate. The extract was washed with sodium bicarbonate solution and water and dried. Evaporation of the solvent gave 23.22 g. of crude product. Chromatography of a 19 g. portion on alumina afforded 7.71 g. of pure 1-hydroxy-3,7-dimethyl-4-(phenylsulfonyl)-9-(2,6,6-trimethylcyclohexen-1-yl)-nona-2,6,8-triene (48% yield) as a pale yellow oil having a UV in isopropanol at λ max= 272–3 mμ (ε=16800).

EXAMPLE 6

Preparation of vitamin A alcohol

A solution of 0.305 g. of 1-hydroxy-3,7-dimethyl-4-(phenylsulfonyl)-9-(2,6,6-trimethylcyclohexen-1-yl)-nona-2,6,8-triene, 1.9 ml. of n-butanol, 0.305 g. of water, and 0.305 g. of potassium hydroxide was refluxed for 80 minutes. The mixture was poured into water and extracted with diethyl ether. The extracts were washed with brine, dried, and concentrated to give 0.203 g. of crude vitamin A alcohol having a UV in isopropanol, λ max =324–5 mμ.

EXAMPLE 7

The vitamin A alcohol produced in Example 6 was dissolved in 2 ml. of pyridine and cooled to −20° to −25°C. and treated with 0.22 ml. of acetyl chloride in 2.5 ml. of dichloromethane. The reaction mixture was stirred for 20 minutes at −20° to −15°C. and then poured into ice water and extracted with diethyl ether. The extracts were washed with 10% aqueous sodium bicarbonate, saturated aqueous cupric sulfate, and brine and dried. Evaporation of the solvent gave 0.195 g. of a yellow oil having a UV in isopropanol, λmax = 324–5 mμ (ε = 19,510). Liquid chromatographic analysis showed that the vitamin A acetate content was 29%.

EXAMPLE 8

Sodamide was prepared by the addition of 0.12 g. of sodium to 4 ml. of ammonia containing a crystal of ferric nitrate. When the blue solution had decolorized 1-hydroxy-3,7-dimethyl-4-(phenylsulfonyl)-9-(2,6,6-trimethylcyclohexen-1-yl)-nona-2,6,8-triene, (0.13 g.) was added at −80°C. in 2 ml. of diethyl ether. The solution was warmed to reflux (−33°C.) and kept there 5 minutes. Ammonium chloride (0.5 g.) was added followed by 15 ml. of diethyl ether. The ammonia was evaporated and the organic solution was washed with brine and dried and concentrated to afford 0.25 g. of an orange oil containing vitamin A alcohol and displaying a UV in isopropanol at λmax = 328 mμ.

Acetylation was carried out as described in Example 7 utilizing 0.2 g. of the crude vitamin A alcohol. This afforded 0.218 g. of crude vitamin A acetate having a UV in isopropanol at λ max = 325–7 (ε = 21,180). Liquid chromatography indicated a vitamin A acetate content of 29%.

EXAMPLE 9

1-hydroxy-3,7-dimethyl-4-(phenylsulfonyl)-9-(2,6,6-trimethylcyclohexen-1-yl)-nona-2,6,8-triene, (0.295 g.) was dissolved in 2.0 ml. of t-butanol and 0.6 g. of potassium t-butoxide was added. The mixture was then stirred for ½ hour at room temperature, refluxed for 1 hour and poured into water. The aqueous mixture was extracted with diethyl ether and washed with brine and dried to give 0.242 g. of crude vitamin A alcohol.

Acetylation of the crude vitamin A alcohol was carried out by the procedure of Example 7 to afford 0.195 g. of crude vitamin A acetate having a UV in isopropanol at λ max = 320–2 mμ (ε = 18,200).

EXAMPLE 10

Sodamide was prepared by the addition of 0.48 g. of sodium to 20 ml. o anhydrous ammonia containing a crystal of ferric nitrate. When the color was discharged, a solution of 0.54 g. of 1-hydroxy-3,7-dimethyl-4-(phenylsulfonyl)-9-(2,6,6-trimethylcyclohexen-1-yl)-nona-2,6,8-triene in 10 ml. of anhydrous diethyl ether was added, followed by 2.15 ml. of t-butanol added in two portions. Total reaction time at −33°C. was 1½ hours. Solid ammonium chloride (2.5 g.) was added and the ammonia was evaporated. Water was added and the residue was extracted with diethyl ether. of combined extracts were washed with brine, dried and concentrated to give 0.399 g. of crude vitamin A alcohol.

Acetylation of the vitamin A alcohol as described in Example 7 afforded 0.364 g. of crude vitamin A acetate having a UV in isopropanol at λmax = 324–4 mμ (ε=22,935). Liquid chromatography indicated a vitamin A acetate content of 47% of which 45% was the all trans isomer.

EXAMPLE 11

Preparation of 1-(p-trifluoromethylphenylsulfonyl)-2-methyl-4-acetoxy-but-2-ene

To a solution of 4-bromobenzotrifluoride (34.2 g.) in diethyl ether at −20° to −25°C. was added over 25 minutes 71 ml. of a 1.95 M solution of n-butyllithium in hexane. After stirring an additional 20 minutes at −20°C., a solution of 20 g. of sulfur dioxide in 50 ml. of diethyl ether was added over 10 minutes at −20° to −30°C. The suspension was allowed to come to room temperature over 45 minutes and the lithium p-trifluoromethylphenyl sulfinate was isolated by centrifugation. The solid was slurried with 200 ml. of diethyl ether and recentrifuged, collected and dried under vacuum. The product had m.p. 259.5°–264.5°C. and analyzed for 84% sulfinic acid salt.

A mixture of the sulfinic acid salt (26.0 g.) and 1-chloro-2-methyl-4-acetoxy-but-2-ene (9.75 g.) in 125 ml. of dimethylformamide was heated to 60°C. for 3¾ hours, cooled, poured into 1.2 l. of water and extracted with ethyl acetate. The extracts were washed with water and brine and dried. Removal of the solvent afforded 18.72 g. of the desired product. Chromatography of a 3.5 g. portion on silica gel gave 3.25 g. of the 1-(p-trifluoromethylphenylsulfonyl)-2-methyl-4-acetoxy-but-2-ene as a colorless oil. Anal. calcd. for $C_{14}H_{15}F_3O_4S$: C 50.00, H 4.50, S 9.53; found C 49.77, H 4.68, S 9.71%.

EXAMPLE 12

Preparation of 1-(p-trifluoromethylphenylsulfonyl)-2-methyl-4-hydroxy-but-2-ene

To a suspension of 1.02 g. of lithium aluminum hydride in 100 ml. of tetrahydrofuran (THF) at −25°C. was added 15.0 g. of 1-(p-trifluoromethylphenylsulfonyl)-2-methyl-4-acetoxy-but-2-ene in 50 ml. of THF over a 20 minute period. The temperature was maintained at −20° to −30°C. and following the addition the mixture was stirred 45 minutes at −20°C. The reaction was quenched by the addition of 18 ml. of saturated magnesium sulfate solution and the solution dried over anhydrous magnesium sulfate. The mixture was filtered, the THF removed at reduced pressure, and the residue dissolved in 200 ml. of ethyl acetate, dried, and concentrated to give 12.18 g. of 1-(p-trifluoromethylphenylsulfonyl)-2-methyl-4-hydroxy-but-2-ene as a low melting solid.

EXAMPLE 13

Preparation of 1-hydroxy-3,7-dimethyl-4-(p-trifluoromethylphenylsulfonyl)-9-(2,6,6-trimethylcyclohexen-1-yl)-nona-2,6,8-triene The 1-(p-trifluoromethylphenylsulfonyl)-2-methyl-4-hydroxy-but-2-ene, (1.0 g.) was dissolved in 10 ml. of tetrahydrofuran (THF) and the solution coold to −70°C. n-butyllithium (2.9 ml., 2.35 M) was added dropwise over 15 minutes and the solution stirred at −70°C. for 40 minutes. A solution of 1-chloro-3-methyl-5-(2,6,6-trimethylcyclohexen-1-yl)-penta-2,4-diene (1.30 g.) in 5 ml. of THF was added and the reaction mixture stirred at −65° to −70°C. for 55 minutes and allowed to warm to 0°C. over 15 minutes. The mixture was then poured onto ice and 4% by weight aqueous HCl and extracted with diethyl ether. The extracts were washed with sodium bicarbonate solution and brine and dried. Evaporation of the solvent gave 2.2 g. of the crude 1-hydroxy-3,7-dimethyl-4-(p-trifluoromethylphenylsulfonyl)-9-(2,6,6-trimethylcyclohexen-1-yl)-nona-2,6,8-triene. chromatography of the crude product on silica gel proceeded with some decomposition, but still afforded 0.059 g. of pure 1-hydroxy-3,7-dimethyl-4-(p-trifluoromethylphenylsulfonyl)-9-(2,6,6-trimethylcyclohexen-1-yl)-nona-2,6,8-triene (3.5% yield) having a UV in isopropanol at λmax = 264–6, 270–72 mμ.

This example demonstrates that the use of a phenyl sulfone derivative where the phenyl group is substituted with an electron withdrawing substituent such as trifluoromethyl produces trace amounts of the alkylated nona-2,6,8-triene.

EXAMPLE 14

Preparation of vitamin A acetate

Sodamide was prepared by dissolving 0.014 g. of sodium to 5 ml. of ammonia containing a crystal of ferric nitrate. To the decolorized suspension was added 0.89 g. of t-butanol followed by a solution of 0.030 g. of the 1-hydroxy-3,7-dimethyl-4-(p-trifluoromethylphenylsulfonyl)-9-(2,6,6-trimethylcyclohexen-1-yl)-nona-2,6,8-triene in 20 ml. of diethyl ether. The reaction mixture was stirred for 1½ hours at reflux and 0.5 g. of ammonium chloride was added followed by 5 ml. of diethyl ether. The ammonia was evaporated and the residue was added to water and extracted with diethyl ether. The extracts were washed with brine and dried and concentrated to give 0.016 g. of a yellow oil containing vitamin A alcohol.

The crude vitamin A alcohol product was acetylated by the procedure of Example 7 to give 0.011 g. of crude vitamin A acetate product which had a UV absorption in isopropanol at λmax = 323–7. Liquid chromatographic analysis showed that the ratio of all-trans to 11-cis vitamin A acetate was 7:1 and that the total vitamin A acetate content was 1.5% (a 0.5% yield based on the 1-hydroxy-3,7-dimethyl-4-(p-trifluoromethylphenylsulfonyl)-9-(2,6,6-trimethyl-cyclohexen-1-yl)-nona-2,6,8-triene.

EXAMPLE 15

Preparation of 1-(p-methoxyphenylsulfonyl)-2-methyl-4-acetoxy-but-2-ene

To a solution of p-bromoanisole (1.96 g.) in diethyl ether at −15° to −20°C. was added 4.25 ml. of a 2.30 M solution of n-butyllithium in hexane. The solution was stirred for 2 hours at −15° to −20°C. and 1.28 ml. of sulfur dioxide in 10 ml. of diethyl ether was added at −25°C. to −30°C. The suspension was then allowed to warm to room temperature, was filtered, washed with diethyl ether, and the solid lithium p-methoxyphenylsulfinate (1.20 g.) collected and dried.

The crude lithium p-methoxyphenylsulfinate (7.15 g.) and 1-chloro-2-methyl-4-acetoxy-but-2-ene (3.23 g.) were mixed with 60 ml. of dimethylformamide and heated to 60°–65°C. for 5 hours. A second portion of lithium p-methoxyphenylsulfinate (0.85 g.) was added and heating continued for 3 hours. The mixture was then poured onto ice and water and was extracted with ethyl acetate. The extracts were washed with brine, dried, and concentrated to give 6.3 g. of crude 1-(p-methoxyphenylsulfonyl)-2-methyl-4-acetoxy-but-2-ene. A 3.3 g. portion was chromatographed on silica gel to give 1.4 g. of pure sulfone acetate as an oil. Crystallization from diethyl ether gave the analytically pure 1-(p-methoxyphenylsulfonyl)-2-methyl-4-acetoxy-but-2-ene, m.p. 54°–56°C.

EXAMPLE 16

Preparation of 1-(p-methoxyphenylsulfonyl)-2-methyl-4-hydroxy-but-2-ene

To a suspension of 0.38 g. of lithium aluminum hydride in 25 ml. of tetrahydrofuran (THF) there was added at −20°C. to −25°C. a solution of 2.98 g. of 1-(p-methoxyphenylsulfonyl)-2-methyl-4-acetoxy-but-2-ene in 5 ml. of THF. The mixture was stirred at −20°C. to −25°C. for 45 minutes and quenched with saturated sodium sulfate solution. The mixture was filtered, dried, and concentrated to give 2.45 g. of 1-(p-methoxyphenylsulfonyl)-2-methyl-4-hydroxy-but-2-ene which solidified upon standing in the freezer.

EXAMPLE 17

Preparation of 1-hydroxy-3,7-dimethyl-4-(p-methoxyphenylsulfonyl)-9-(2,6,6-trimethylcyclohexen-1-yl)-nona-2,6,8-triene To a solution of 1.28 g. of 1-(p-methoxyphenylsulfonyl)-2-methyl-4-hydroxy-but-2-ene in 15 ml. of tetrahydrofuran (THF) was added at −70°C. 4.25 ml. of 2.37 M solution of n-butyllithium in hexane. The mixture was stirred at −70°C. for 30 minutes and a solution of 1.78 g. of 1-chloro-3-methyl-5-(2,6,6-trimethylcyclohexen-1-yl)-penta-2,4-diene in 5 ml. of THF was added at −70°C. The solution was stirred at −70°C. for 50 minutes and allowed to warm to 70°C. The mixture was poured into water and extracted with diethyl ether. The extracts were washed with water, dried and concentrated to give 2.6 g. of 1-hydroxy-3,7-dimethyl-4-(p-methoxyphenyl-sulfonyl)-9-(2,6,6-trimethylcyclohexen-1-yl)-nona-2,6,8-triene which was chromatographed on silica get to give 0.48 g. of 1-hydroxy-3,7-dimethyl-4-p-methoxyphenylsulfonyl)-9-(2,6,6-trimethylcyclohexen-1-yl)-nona-2,6,8-triene (20% yield) having a UV in isopropanol at λmax = 241–2 mμ (ε24,625).

EXAMPLE 18

Preparation of vitamin A acetate

Sodamide was prepared by the addition of 0.33 g. of sodium to 10 ml. of anhydrous ammonia containing a crystal of ferric nitrate. When the color was discharged, a solution of 0.31 g. of 1-hydroxy-3,7-dimethyl-4-(p-methoxyphenylsulfonyl)-9-(2,6,6-trimethylcyclohexen-1-yl)-nona-2,6,8-triene in 5 ml. of diethyl ether was added followed by 2.5 ml. of t-butanol. The mixture was allowed to reflux (−33°C.) for 1 hour and was poured into ice water. The mixture was extracted with diethyl ether, and the extracts were washed with brine, dried, and concentrated to give 0.24 g. of crude vitamin A alcohol having a UV in isopropanol at λmax = 324–5 mμ. Acetylation of the total crude alcohol as described in Example 7 afforded 0.185 g. of crude vitamin A acetate having a UV in isopropanol at λmax = 324–5 mμ (ε=31,145). Liquid chromatography indicated a vitamin A acetate content of 58% by weight.

Repetition of the above sequence on a larger scale utilizng 0.68 g. of 1-hydroxy-3,7-dimethyl-4-(p-methoxyphenylsulfonyl)-9-(2,6,6-trimethylcyclohexen-1-yl)-nona-2,6,8-triene gave 0.42 g. of crude vitamin A acetate which contained 73% by weight of vitamin A acetate by liquid chromatography which was approximately 100% of the trans isomer.

EXAMPLE 19

Preparation of 1-(4-N,N-dimethylaminophenylsulfonyl)-2-methyl-4-acetoxy-but-2-ene To a suspension of sodium 4-N,N-dimethylaminophenylsulfinate (8.40 g.) in 50 ml. of dimethylformamide (DMF) was added 5.20 g. of 1-chloro-2-methyl-4-acetoxy-but-2-ene dissolved in 10 ml. of DMF. The mixture was stirred and heated at 60°C. for 4½ hours, cooled, poured into 600 ml. of water, and extracted with ethyl acetate. The extracts were washed with brine, dried, and concentrated to give a yellow solid 1-(4-N,N-dimethylaminophenylsulfonyl)-2-methyl-4-acetoxy-but-2-ene (9.88 g.). Recrystallization from ethanol gave 1-(4-N,N-dimethylaminophenylsulfonyl)-2-methyl-4-acetoxy-but-2-ene as analytically pure crystals, m.p. 82°–84°C.

EXAMPLE 20

Preparation of 1-(4-N,N-dimethylaminophenylsulfonyl)-2-methyl-4-hydroxy-but-2-ene.

To a stirred suspension of 0.645 g. of lithium aluminum hydride (LAH) in 58 ml. of tetrahydrofuran (THF) at −20°C. to −30°C. was added a solution of 8.84 g. of 1-(4-N,N-dimethylaminophenylsulfonyl)-2-methyl-4-acetoxy-but-2-ene in 30 of THF. The reaction mixture was stirred for 30 minutes at −20°C., then at −10°C. for 30 minutes at which time an additional 0.2 g. of LAH was added at −3°C. To suspension was stirred for 15 minutes at −5°C., warmed to 0°C. and the reaction quenched by the addition of saturated magnesium sulfate solution. Solid magnesium sulfate was added and the mixture was filtered. Removal of the solvent at reduced pressure afforded 7.25 g. of 1-(4-N,N-dimethylaminophenylsulfonyl)-2-methyl-4-hydroxy-but-2-ene as a colorless solid. Recrystallization from ethyl acetate and ethanol gave analytically pure 1-(4-N,N-dimethylaminophenylsulfonyl)-2-methyl-4-hydroxy-but-2-ene, m.p. 160°–164°C.

EXAMPLE 21

Preparation of 1-hydroxy-3,7-dimethyl-4-(4-N,N-dimethylaminophenylsulfonyl)-9-(2,6,6-trimethylcyclohexen-1-yl)-nona-2,6,8-triene A solution of n-butyllithium in hexane (11.3 ml., 2.30 M) was added over 20 minutes at −70°C. to a solution of 3.50 g. of 1-(4-N,N-dimethylaminophenylsulfonyl)-2-methyl-4-hydroxy-but-2-ene in 68 ml. of tetrahydrofuran (THF). The reaction mixture was stirred at −70°C. for 45 minutes and a solution of 1-chloro-3-methyl-5-(2,6,6-trimethylcyclohexen-1-yl)-penta2,4-diene (4.7 g.) in 10 ml. of THF was added at −70°C. over 15 minutes. The mixture was stirred 1½ hours at −70°C. and was then warmed to 0°C. and poured onto ice water. The mixture was extracted with ethyl acetate and the extracts were washed with brine, dried, and concentrated to give 7.8 g. of 1-hydroxy-3,7-dimethyl-4-(4-N,N-dimethylaminophenylsulfonyl)-9-(2,6,6-trimethylcyclohexen-1-yl)-nona-2,6,8-triene. Chromatography on silica gel of a 6.9 g. portion gave 3.08 g. of pure 1-hydroxy-3,7-dimethyl-4-(4-N,N-dimethylaminophenylsulfonyl)-9-(2,6,6-trimethylcyclohexen-1-yl)-nona-2,6,8-triene (57% yield) which had a UV in isopropanol at $\lambda$ max = 284 m$\mu$ ($\epsilon$=35,800).

EXAMPLE 22

Preparation of vitamin A acetate

Sodamide was prepared by the addition of 0.33 g. of sodium to 10 ml. of ammonia containing a crystal of ferric nitrate. When the solution had decolorized, 2.5 ml. of t-butanol, and a solution of the 0.326 g. of 1-hydroxy-3,7-dimethyl-4-(4-N,N-dimethylaminophenylsulfonyl)-9-(2,6,6-trimethylcyclohexen-1-yl)-nona-2,6,8-triene in 5 ml. of diethyl ether was added. After stirring at −33°C. for 1½ hours, the mixture was treated with ammonia chloride and the ammonia evaporated. The residue was taken up in diethyl ether and water and the mixture extracted with diethyl ether. The extracts were dried and concentrated to give 0.224 g. of crude vitamin A alcohol. Acetylation of the crude vitamin A alcohol as described in Example 7 afforded 0.210 g. of vitamin A acetate having a UV in isopropanol at $\lambda$max = ($\epsilon$=34,600). Liquid chromatography indicated a vitamin A acetate content of 57% by weight and an all trans content of 94% .

EXAMPLE 23

Trans-1-p-toluenesulfonyl-2-methyl-4-acetoxy-but-2-ene

To a mechanically stirred suspension of 273.0 g. (1.54 moles) of sodium p-toluenesulfinate in 1100 ml. of dry dimethylformamide was added 215.4 g. (1.33 moles) of isoprene chloroacetate. The mixture was heated under argon at 60°C. for 4.75 hours and was concentrated in vacuo to a volume of ca. 300 ml. The suspension was poured into 3 liters of ice water and stirred for 10 minutes while the product precipitated. The solid was removed by filtration and the filter cake was dissolved in 900 ml. of ethyl acetate and was dried (MgSO$_4$). Removal of the solvent gave 357.0 g. (95%) trans-1-p-toluenesulfonyl-2-methyl-4-acetoxy-but-2-ene as a light yellow, low melting solid (purity >95% by nmr). Two recrystalllizations from methanol of a sample from a similar preparation gave colorless crystals, m.p. 56.5°–59°C. of trans-1-p-toluenesulfonyl-2-methyl-4-acetoxy-but-2-ene.

EXAMPLE 24 trans-1-(p-toluenesulfonyl)-2-methyl-4-hydroxy-but-2-ene

A solution of 194 g. (1.83 moles) of sodium carbonate in 555 ml. of water was added in four portions to a stirred, cooled solution of 346.8 g. (1.22 moles) of trans-1-p-toluenesulfonyl-2-methyl-4-acetoxy-but-2-ene maintaining a temperature of 0° to 5°C. The mixture was stirred for 4.25 hours and was filtered to remove sodium acetate. The filtrate was concentrated to a 600 ml. volume on a rotary evaporator, was diluted with 2000 ml. of water and was extracted with three 700 ml portions of ethyl acetate. The combined extracts were washed with two 2000 ml-portions of brine and dried (MgSO$_4$) and concentrated to give 288 g. (97%) trans-1-(p-toluenesulfonyl)-2-methyl-4-hydroxy-but-2-ene as a crude white solid (>80% pure by nmr). Recrystallization from 1800 ml. of diethyl ether and 50 ml. of ethyl acetate gave 198.8 g. (68.6%) of trans-1-(p-toluenesulfonyl)-2-methyl-4-hydroxy-but- 2-ene as colorless crystals in two crops. The mother liquor (89 g.) was ca. 60% trans-1-(p-toluenesulfonyl)-2-methyl-4-hydroxy-but-2-ene by nmr. Recrystallization of a portion of the first crop from diethyl ether afforded pure trans-1-(p-toluenesulfonyl)-2-methyl-4-hydroxy-but-2-ene m.p. 62.5°–65°C.

EXAMPLE 25

Preparation of 1-hydroxy-3,7-dimethyl-4-p-toluenesulfonyl-9-(2,6,6-trimethyl-cyclohexen-1-yl)-nona-2,6,8-triene Lithium diisopropylamide was prepared by the addition of 20 ml. of a 2.35 M butyllithium solution in hexane to a −70°C. solution of 4.75 g. of diisopropylamine in 45 ml. of tetrahydrofuran. After the addition was complete (30 minutes) the solution was allowed to warm to 0°C. and was stirred at 0°C. for one hour.

The lithium diisopropylamide solution was then added over a 75 minute period to a −70°C. solution of 5.0 g. of 1-p-toluenesulfonyl-2-methyl-4-hydroxy-but-2-ene and 7.0 g. of 1-bromo-3-methyl-5-(2,6,6-trimethylcyclohexen-1-yl)-penta-2,4-diene in 50 ml. of tetrahydrofuran. After the addition, the reaction mixture was stirred for an additional 45 minutes at −70°C. and was then warmed to 0°C. and was poured onto 400 ml. of ice water. The mixture was extracted with three 300 ml. portions of diethyl ether, and the combined extracts were washed with two 400 ml. portions of brine and dried over anhydrous magnesium sulfate. Evaporation of the solvent at reduced pressure gave a yellow oil which was immediately chromatographed on 300 g. of silica gel eluting with 5 to 30% diethyl ether in benzene followed by ethyl acetate. From the chromotography there was obtained 6.43 g. of pure 1-hydroxy-3,7- dimethyl-4-p-toluenesulfonyl-9 -(2,6,6-trimethylcyclohexen-1-yl)-nona-2,6,8-triene (70% yield) and 1.21 g. of recovered hydroxysulfone starting material. The product had UV in isopropanol at λmax = 228–9 mμ ( of the C-20 sulfone in each of these examples is set forth in the following table. In the following table, yield is calculated on the basis of C-5-hydroxy sulfone starting material.

TABLE

| Ex. | C-15 Halide | mMoles of C-15 Halide | mMoles of C-15 Hydroxy Sulfone | Base | mMoles of Base | Solvents | Mode of Addition | % Yield of C-20 Sulfone |
|---|---|---|---|---|---|---|---|---|
| 27 | Chloride | 19.7 | 13.0 | butyl lithium | 26.0 | tetrahydrofuran & n-hexane | chloride to dianion | 41% |
| 28 | Bromide | 4.9 | 2.2 | lithium diisopropyl amide | 8.3 | tetrahydrofuran n-hexane & diethyl ether | base to substrate | 82% |
| 29 | Chloride | 4.6 | 1.8 | lithium diisopropyl amide | 8.32 | tetrahydrofuran & n-hexane | base to substrate | 38% |
| 30 | Chloride | 5.74 | 4.2 | lithium diisopropyl amide | 9.8 | n-hexane & tetrahydrofuran | base to substrate | 50% |
| 31 | Bromide | 5.23 | 4.2 | lithium diisopropyl amide | 9.4 | diisopropyl amine, diethyl ether & tetrahydrofuran | base to substrate | 36% |
| 32 | Bromide | 11.4 | 8.3 | lithium diisopropyl amide | 19.7 | diisopropyl amine, diethyl ether & tetrahydrofuran | base to substrate | 52% |
| 33 | Bromide | 25.0 | 21.0 | lithium diisopropyl amide | 44.0 | tetrahydrofuran & diethyl ether | bromide to dianion | 90% |
| 34 | Bromide | 25.0 | 21.0 | lithium diisopropyl amide | 44.0 | tetrahydrofuran | base to substrate | 84% |
| 35 | Bromide | 11.4 | 8.3 | lithium diethyl amide | 19.7 | tetrahydrofuran | base to substrate | 68% |
| 36 | Bromide | 6.85 | 4.2 | sodium amide | 9.4 | tetrahydrofuran & liquid NH₃ | bromide to dianion | 44% |
| 37 | Bromide | 5.5 | 4.2 | potassium tertiary amyl oxide | 9.6 | tetrahydrofuran | bromide to dianion | 10% to 20% |
| 38 | Bromide | 5.5 | 4.2 | potassium tertiary amyl oxide | 9.6 | tetrahydrofuran | base to substrate | 14.4% |
| 39 | Bromide | 5.3 | 4.2 | dimsyl sodium | 9.6 | tetrahydrofuran | base to substrate | 20% to 30% |

ε = 25,740); 260–2 mμ ( ε = 17,070) and 274–5 mμ ( ε = 15,010).

EXAMPLE 26

Preparation of Vitamin A acetate to a solution of 0.282 g. of sodamide in 20 ml. of anhydrous ammonia at −33°C. was added 1.25 ml. of t-butanol. To the solution was added 0.600 g. of 1-hydroxy-3,7-dimethyl-4-p-toluenesulfonyl-9-(2,6,6-trimethylcyclo-1-yl)-nona-2,6,8-triene in 10 ml. of diethyl ether over 10 minutes. The solution was allowed to reflux for one hour and was quenched by the addition of 1.0 g. of ammonium chloride. Diethyl ether (20 ml.) was added and the ammonia was evaporated. The residual mixture was poured into 40 ml. of ice water and was extracted with diethyl ether. The combined extracts were washed with brine and dried and concentrated to afford 0.432 g. of crude vitamin A alcohol. Acetylation of the total crude vitamin A alcohol with 0.27 g. of acetic anhydride and 0.203 g. of triethylamine in 1.4 ml. of hexane afforded 0.413 g. of vitamin A acetate as an oil having a UV in isopropanol at λ max = 325–7mμ (ε = 43,000). Liquid chromatography of the oil indicated a vitamin A acetate content of 75.2% by weight and an all trans content of 100%.

EXAMPLES 27–39

In the following examples, trans 1-p-toluenesulfonyl-2-methyl-4-hydroxy-but-2-ene [C-5 hydroxysulfone] was reacted with 1-halo-3-methyl-5-(2,6,6-trimethylcyclohexen-1-yl)-penta-2,4-diene [C-15 halide] to produce 1-hydroxy-3,7-dimethyl-4-p-toluenesulfonyl-9-(2,6,6-trimethylcyclohexen-1-yl)-nona-2,6,8-triene [C-20 sulfone] utilizing the conditions set forth in Example 25. Any departure from the conditions set forth in Example 25 is given in the following table. The yield

We claim:
1. A process for producing a compound of the formula:

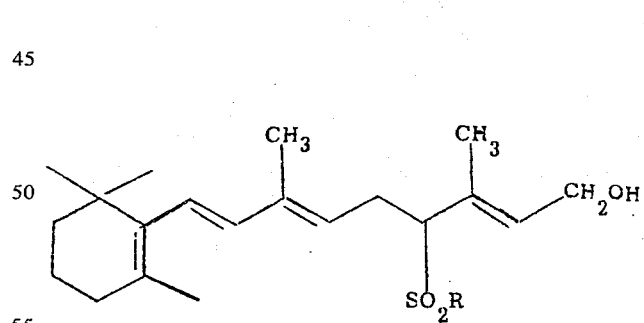

wherein
R is unsubstituted aryl, or aryl substituted with an electron donating group;

comprising condensing a sulfone of the formula:

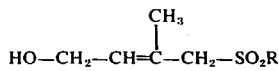

wherein
R is as above; with a derivative of the formula:

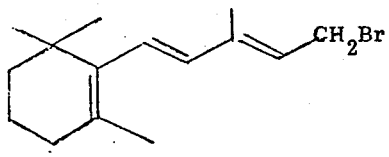

in an inert polar organic solvent medium in the presence of a compound of the formula:

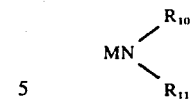

wherein
M is an alkali metal and
$R_{10}$ and $R_{11}$ are independently lower alkyl.

2. The process of claim 1 wherein R is phenyl or phenyl substituted with lower alkyl, hydroxy, lower alkoxy, phenoxy or

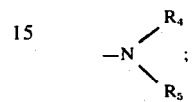

and $R_4$ and $R_5$ are hydrogen or lower alkyl.

* * * * *